(12) United States Patent
Kim et al.

(10) Patent No.: US 11,751,814 B2
(45) Date of Patent: Sep. 12, 2023

(54) APPARATUS AND METHOD FOR ESTIMATING BIOLOGICAL INFORMATION, AND ELECTRONIC DEVICE INCLUDING THE SAME

(71) Applicants: SAMSUNG ELECTRONICS CO., LTD., Suwon-si (KR); POSTECH Research and Business Development Foundation, Pohang-si (KR)

(72) Inventors: Young Soo Kim, Seoul (KR); Sung-Min Park, Seoul (KR); Youn Ho Kim, Hwaseong-si (KR); Vega Pradana Rachim, Pohang-si (KR); Sang Yun Park, Hwaseong-si (KR); JinHyeok Baek, Seoul (KR)

(73) Assignees: SAMSUNG ELECTRONICS CO., LTD., Suwon-si (KR); POSTECH Research and Business Development Foundation, Pohang-si (KR)

( * ) Notice: Subject to any disclaimer, the term of this patent is extended or adjusted under 35 U.S.C. 154(b) by 126 days.

(21) Appl. No.: 17/317,524

(22) Filed: May 11, 2021

(65) Prior Publication Data

US 2022/0240863 A1 Aug. 4, 2022

(30) Foreign Application Priority Data

Feb. 4, 2021 (KR) .......................... 10-2021-0016076

(51) Int. Cl.
*A61B 5/00* (2006.01)
*A61B 5/0205* (2006.01)
(Continued)

(52) U.S. Cl.
CPC ............ *A61B 5/7203* (2013.01); *A61B 5/021* (2013.01); *A61B 5/02007* (2013.01);
(Continued)

(58) Field of Classification Search
CPC .............. A61B 5/7203; A61B 5/02007; A61B 5/02055; A61B 5/021; A61B 5/02405;
(Continued)

(56) References Cited

U.S. PATENT DOCUMENTS 9,713,428 B2   7/2017 Chon et al.
10,398,327 B2   9/2019 Estepp et al.
(Continued)

FOREIGN PATENT DOCUMENTS

JP   2018519889 A   *  7/2018
KR   100880392 B1       1/2009
(Continued)

OTHER PUBLICATIONS

Nam, Y., et al., "Respiratory Rate Estimation from the Built-in Cameras of Smartphones and Tablets", Annals of Biomedical Engineering, vol. 42, No. 4, Apr. 2014, pp. 885-898.
(Continued)

*Primary Examiner* — Carl H Layno
*Assistant Examiner* — Michael J Lau
(74) *Attorney, Agent, or Firm* — Sughrue Mion, PLLC

(57) ABSTRACT

An apparatus for estimating biological information of a user may include a light source configured to emit light to an object of the user; an image sensor comprising a pixel array, and configured to acquire successive image frames by detecting light scattered or reflected from the object of the user; and a processor configured to: select a predetermined number of pixel-rows from among pixel-rows of the image sensor, detect signal intensities in the predetermined number of pixel-rows for each image frame of the successive image frames, correct the signal intensities, combine the signal intensities for each image frame of the successive image frames based on correcting the signal intensities, acquire a photoplethysmogram (PPG) signal based on combining the
(Continued)

signal intensities, and estimate the biological information of the user based on the PPG signal.

18 Claims, 15 Drawing Sheets

(51) Int. Cl.
*A61B 5/02* (2006.01)
*A61B 5/024* (2006.01)
*A61B 5/021* (2006.01)
*A61B 5/1455* (2006.01)
*A61B 5/16* (2006.01)

(52) U.S. Cl.
CPC ...... *A61B 5/02055* (2013.01); *A61B 5/02405* (2013.01); *A61B 5/02416* (2013.01); *A61B 5/14551* (2013.01); *A61B 5/165* (2013.01); *A61B 5/4872* (2013.01)

(58) Field of Classification Search
CPC . A61B 5/02416; A61B 5/14551; A61B 5/165; A61B 5/4872
USPC .......................................................... 600/301
See application file for complete search history.

(56) References Cited

U.S. PATENT DOCUMENTS

| | | | |
|---|---|---|---|
| 10,878,216 | B2 | 12/2020 | Kang et al. |
| 11,295,109 | B2 | 4/2022 | Kang et al. |
| 2011/0125034 | A1* | 5/2011 | Tsuji ............... A61B 8/0891 600/485 |
| 2013/0085355 | A1* | 4/2013 | Timm ............... A61B 5/029 600/479 |
| 2017/0071516 | A1 | 3/2017 | Bhagat et al. |
| 2020/0019745 | A1* | 1/2020 | Kang ............... A61B 5/02427 |
| 2020/0221960 | A1* | 7/2020 | Jang ............... A61B 5/7242 |
| 2020/0260956 | A1 | 8/2020 | Lee et al. |
| 2020/0359900 | A1* | 11/2020 | Yan ............... A61B 5/02416 |
| 2022/0043997 | A1 | 2/2022 | Kang et al. |

FOREIGN PATENT DOCUMENTS

| | | | | |
|---|---|---|---|---|
| KR | 101026046 | B1 * | 3/2011 | ............. H04N 5/357 |
| KR | 1020130093925 | A | 8/2013 | |
| KR | 1020150016903 | A | 2/2015 | |
| KR | 1020160075677 | A | 6/2016 | |
| KR | 11020170004804 | A | 1/2017 | |
| KR | 1020170032877 | A | 3/2017 | |
| KR | 101725357 | B1 | 4/2017 | |
| KR | 1020190050725 | A | 5/2019 | |
| KR | 102055041 | B1 | 12/2019 | |
| KR | 20190142891 | A * | 12/2019 | ......... A61B 5/14552 |
| KR | 10-2020-0007312 | A | 1/2020 | |
| KR | 102108961 | B1 | 5/2020 | |

OTHER PUBLICATIONS

McDuff, D., et al., "Fusing Partial Camera Signals for Noncontact Pulse Rate Variability Measurement", IEEE Transactions on Biomedical Engineering, vol. 65, No. 8, 2017, 3 pages.

Rapczynski, M., et al., "Effects of Video Encoding on Camera-Based Heart Rate Estimation", IEEE Transactions on Biomedical Engineering, vol. 66, No. 12, Dec. 2019, pp. 3360-3370.

McDuff, D., et al., "A Survey of Remote Optical Photoplethysmographic Imaging Methods", ResearchGate, Aug. 2015, pp. 6398-6404 (8 pages).

Sun, Y. et al., "Photoplethysmography Revisited: From Contact to Noncontact, From Point to Imaging" IEEE Transactions on Biomedical Engineering, vol. 00, No. 0, 2015, pp. 1-15 (16 pages).

Choi, A., et al., "Photoplethysmography sampling frequency: pilot assessment of how low can we go to analyze pulse rate variability with reliability?", Physiological Measurement 38.3, iopscience.iop.org, 2017, pp. 1-19 (20 pages).

Fujita, D., et al., "Evaluation of the Possible Use of PPG Waveform Features Measured at Low Sampling Rate", IEEE Access, vol. 7, 2019, pp. 58361-58367.

Sun, Y., et al., "Noncontact imaging photoplethysmography to effectively access pulse rate variability", Journal of Biomedical Optics, vol. 18, No. 6, Jun. 2013, pp. 061205-1 to 061205-9 (11 pages).

Communication dated Oct. 21, 2022 by the Korean Intellectual Property Office for Korean Patent Application No. 10-2021-0016076.

* cited by examiner

APPARATUS AND METHOD FOR ESTIMATING BIOLOGICAL INFORMATION, AND ELECTRONIC DEVICE INCLUDING THE SAME

CROSS-REFERENCE TO RELATED APPLICATION(S)

This application is based on and claims priority under 35 U.S.C. § 119 to Korean Patent Application No. 10-2021-0016076, filed on Feb. 4, 2021, in the Korean Intellectual Property Office, the disclosure of which is incorporated by reference herein in its entirety.

BACKGROUND

1. Field

The disclosure relates to an apparatus and method for estimating biological information.

2. Description of Related Art

As medical science has progressed and average life expectancy has increased, an interest in health care has increased. Also, interest in medical equipment/devices has increased to extend not only to various types of medical equipment used in hospitals or health examination facilities, but also to middle-sized or small-sized types of medical equipment provided for use in public facilities and compact medical equipment and health-care apparatuses that may be kept at home or carried by individuals. Medical devices for measuring biological information may be broadly classified into invasive devices and non-invasive devices. Non-invasive devices may detect biological information in a relatively simple manner without causing pain to a subject. However, the accuracy and precision of the detection results is not high and thus a great deal of research is being conducted to overcome this drawback.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of the disclosure, an apparatus for estimating biological information of a user may include a light source configured to emit light to an object of the user; an image sensor comprising a pixel array, and configured to acquire successive image frames by detecting light scattered or reflected from the object of the user; and a processor configured to: select a predetermined number of pixel-rows from among pixel-rows of the image sensor, detect signal intensities in the predetermined number of pixel-rows for each image frame of the successive image frames, correct the signal intensities, combine the signal intensities for each image frame of the successive image frames based on correcting the signal intensities, acquire a photoplethysmogram (PPG) signal based on combining the signal intensities, and estimate the biological information of the user based on the PPG signal.

The processor may calculate a signal-to-noise ratio (SNR) of each pixel-row of the image frame, and select the predetermined number of pixel-rows based on the SNR of each pixel-row of the image frame.

The processor may select the predetermined number of pixel-rows in an ascending order or a descending order of magnitudes of the SNR of each pixel-row of the image frame.

The processor may correct an influence of a signal intensity according to a distance between the light source and each of the predetermined number of pixel-rows of the image sensor by using Lambert-Beer's law.

The processor may generate a signal intensity compensation model representing a relationship between the signal intensities and a pixel-row number.

The processor may combine the signal intensities for each frame by using the signal intensity compensation model and a multi-row combine with amplitude compensation (MRAC) algorithm.

The processor may acquire time information based on operating information of each pixel-row of the image sensor, and acquire the PPG signal based on the signal intensities of each image frame and the time information.

The processor may resample the PPG signal, or perform preprocessing to reduce noise by using a filter.

The processor may extract feature points based on the PPG signal, and estimate the biological information based on the feature points.

The biological information may include at least one of oxygen saturation (SpO2), pulse rate variability, blood pressure, arterial stiffness, stress index, body fat, or body temperature.

According to an aspect of the disclosure, a method of estimating biological information of a user may include emitting, by a light source, light to an object of the user; detecting, by an image sensor comprising a pixel array, light scattered or reflected from the object of the user; acquiring, by the image sensor, successive image frames based on detecting the light scattered or reflected from the object of the user; selecting, by a processor, a predetermined number of pixel-rows from among pixel-rows of the image sensor; detecting, by the processor, signal intensities in the predetermined number of pixel-rows for each image frame of the successive image frames; correcting, by the processor, the signal intensities; combining, by the processor, the signal intensities for each image frame of the successive image frames based on correcting the signal intensities; acquiring, by the processor, a photoplethysmogram (PPG) signal based on combining the signal intensities; and estimating, by the processor, the biological information of the user based on the PPG signal.

The selecting of the predetermined number of pixel-rows may include calculating a signal-to-noise ratio (SNR) of each pixel-row of the image frame; and selecting the predetermined number of pixel-rows based on the SNR of each pixel-row of the image frame.

The selecting of the predetermined number of pixels-rows based on the SNR may include selecting the predetermined number of pixels-rows in an ascending order or a descending order of magnitudes of the SNR of each pixel-row of the image frame.

The correcting of the signal intensities may include correcting an influence of a signal intensity according to a distance between the light source and each of the predetermined number of pixel-rows of the image sensor by using Lambert-Beef s law.

The method may include generating a signal intensity compensation model representing a relationship between the signal intensities and a pixel-row number.

The acquiring of the PPG signal by combining the signal intensities for each frame may include combining the signal intensities for each frame by using the signal intensity compensation model and a multi-row combine with amplitude compensation (MRAC) algorithm.

The acquiring of the PPG signal may include acquiring time information based on operating information of each pixel-row of the image sensor; and acquiring the PPG signal based on the signal intensities of each image frame and the acquired time information.

According to an aspect of the disclosure, an electronic device may include a main body; a light source disposed on a surface of the main body, and configured to emit light to an object of a user; a camera module disposed on the surface of the main body, and comprising an image sensor configured to acquire an image frame by detecting light reflected or scattered from the object; and a processor disposed in the main body, and configured to: select a predetermined number of pixel-rows from among pixel-rows of the image sensor, detect signal intensities in the predetermined number of pixel-rows for each image frame of the successive image frames, correct the signal intensities, combine the signal intensities for each image frame of the successive image frames based on correcting the signal intensities, acquire a photoplethysmogram (PPG) signal based on combining the signal intensities, and estimate biological information of the user based on the PPG signal.

The image sensor may acquire an image frame using a rolling shutter technique.

The processor may control the light source to be turned on while the image sensor acquires the image frame, or control the light source using a pulse width modulation scheme.

Other features and aspects will be apparent from the following detailed description, the drawings, and the claims.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
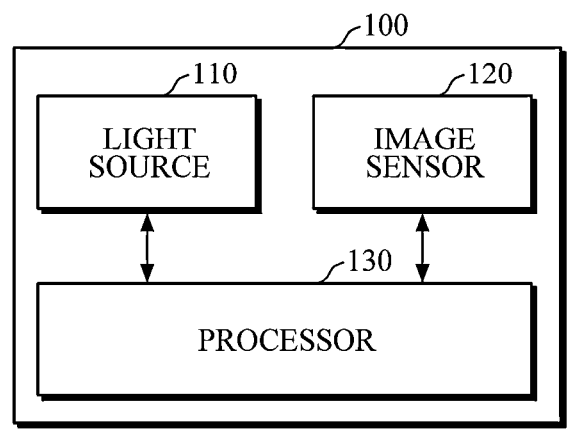
FIG. 1 is a block diagram of an apparatus for estimating biological information according to an example embodiment.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

DETAILED DESCRIPTION

Details of example embodiments are included in the following detailed description and drawings. Advantages and features of the example embodiments, and a method of achieving the same will be more clearly understood from the following example embodiments described in detail with reference to the accompanying drawings. Throughout the drawings and the detailed description, unless otherwise described, the same drawing reference numerals will be understood to refer to the same elements, features, and structures.

It will be understood that, although the terms "first," "second," etc., may be used herein to describe various elements, these elements may not be limited by these terms. These terms are only used to distinguish one element from another. Any references to singular forms of terms may include plural forms of terms unless expressly stated otherwise. In addition, unless explicitly described to the contrary, an expression such as "comprising" or "including" will be understood to imply the inclusion of stated elements but not the exclusion of any other elements. Also, the terms such as "part," "module," etc., may be understood as a unit that performs at least one function or operation and that may be embodied as hardware, software, or a combination thereof.

Hereinafter, example embodiments of an apparatus and method for estimating biological information will be described in detail with reference to the accompanying drawings. The apparatus for estimating biological information may be a medical device used in a specialized medical institution, a smart watch configured to be worn on a wrist of a user, a wearable device (e.g., a smart band-type wearable device, a headphone-type wearable device, a headband type-wearable device, and the like), a mobile device (e.g., a smartphone), a tablet personal computer (PC), and the like, but is not limited thereto.

FIG. 1 is a block diagram of an apparatus for estimating biological information according to an example embodiment.

Referring to FIG. 1, an apparatus 100 for estimating biological information includes a light source 110, an image sensor 120, and a processor 130.

The light source 110 may emit light to an object and may include a light emitting diode (LED), a laser diode (LD), a phosphor, or the like. The light emitted by the light source 110 may include visible light, infrared light, near infrared light, etc. Also, a plurality of light sources 110 may be configured to emit light of the same wavelength or light of different wavelengths from each other. For example, the light source 110 may emit light of green, blue, red, and/or infrared wavelengths, but is not limited thereto.

The light source 110 may be turned on all the time in the process of estimating biological information, or may be driven in a pulse width modulation (PWM) scheme, under the control of the processor 130. The light source 110 may be disposed on the image sensor 120. However, various embodiments of the present disclosure are not limited thereto and an external light source may be used.

The image sensor 120 may be composed of a pixel array, and may be a complementary metal-oxide semiconductor (CMOS) image sensor. However, various embodiments of the present disclosure are not limited thereto. Also, the image sensor 120 may include a plurality of image sensors 120. ISO of the image sensor 120, the exposure time of each pixel, white balance, output resolution, camera focus, and the like, may be set or adjusted in advance.

The image sensor 120 may acquire successive image frames by detecting light scattered or reflected from a user's object using a rolling shutter technique. In general, the rolling shutter technique sequentially scans images for each pixel-row under the control of the processor 130. Hereinafter, a process in which the image sensor 120 acquires image frames through a rolling shutter technique is described with reference to FIGS. 3A and 3B.

Figure 3A:
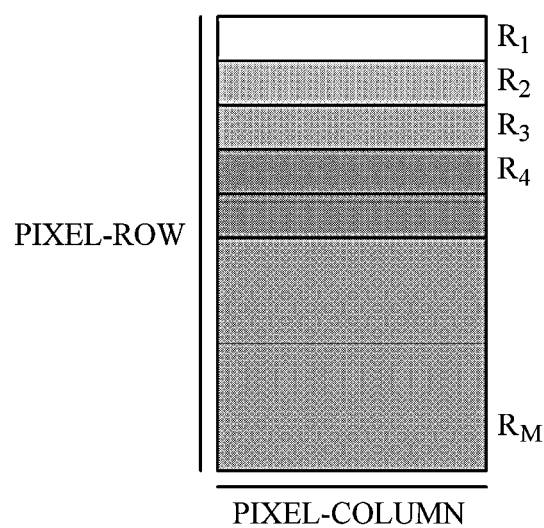
FIGS. 3A and 3B illustrate a process in which an image sensor acquires an image using a rolling shutter technique.
Figure 3B:
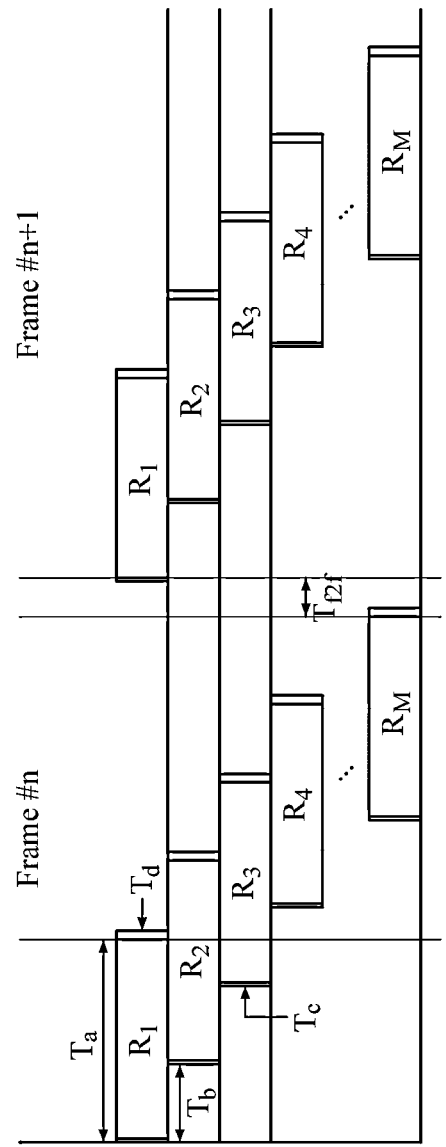

FIGS. 3A and 3B illustrate a process in which the image sensor 120 acquires an image using the rolling shutter technique.

Referring to FIG. 3A, the image sensor 120 includes a plurality of pixel-rows and a plurality of pixel-columns. $R_1$, $R_2$, $R_3$, $R_4$, and $R_M$ in FIG. 3A denote the first pixel-row, the second pixel-row, the third pixel-row, the fourth pixel-row, and the last pixel-row, respectively. In the rolling shutter technique, as shown in FIG. 3A, each pixel-row of the image sensor 120 is sequentially exposed to detect light and scan an image.

Referring to FIG. 3B, a process in which the image sensor 120 scans the $n^{th}$ frame (Frame #n) and the $(n+1)^{th}$ frame (Frame #n+1) by using the rolling shutter technique is illustrated. In the case of the rolling shutter technique, images are sequentially scanned starting from the first row, $R_1$, to the last row, $R_M$, and a scan delay between each pixel-row is $T_b$. In each pixel-row, pixel sensors are exposed for a time of $T_a$ and light reflected or scattered from the object is detected. Each pixel-row undergoes a reset process for a time of $T_c$ before detecting the light, and after detecting the light, it takes a time of $T_d$ to read the detected light. Here, $T_c$ and $T_d$ may be the same. When all pixel-rows from $R_1$ to $R_M$ complete scanning in the $n^{th}$ frame, it takes a time of $T_{f2f}$ to move to the next frame, i.e., the $(n+1)^{th}$ frame, and the image sensor 120 is blocked and does not record any signals during the time of $T_{f2f}$.

When the user's object (e.g., a user's index finger) is in contact with the image sensor 120, the image sensor 120 may be driven by the rolling shutter technique to obtain successive image frames for the object as described above. In this case, the image sensor 120 may include a contact surface that is in contact with the object. The contact surface may be formed as a smooth curved surface, but is not limited thereto.

Alternatively, the image sensor 120 may acquire successive image frames for the object by detecting reflected light without being in contact with the object. A position of the object may be placed vertically or horizontally according to the positions of the light source 110 and the image sensor 120.

Figure 2A:
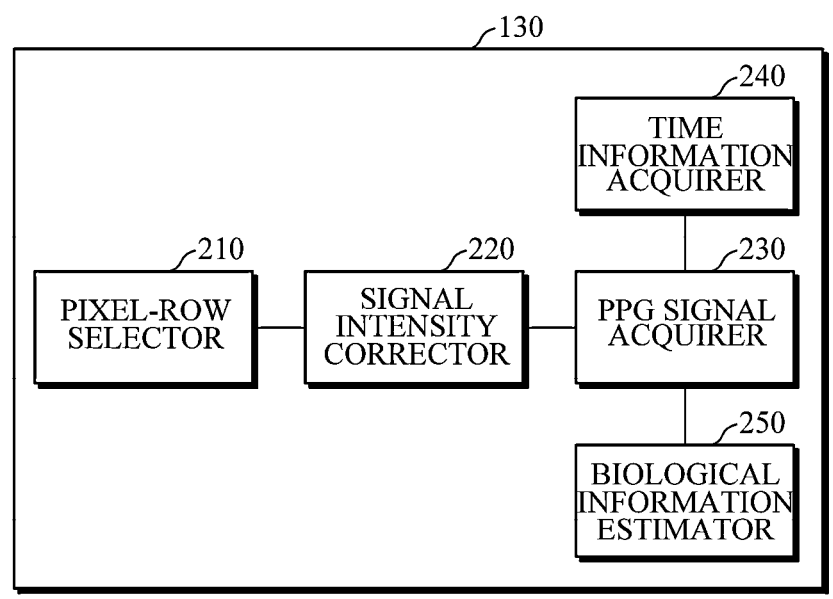
FIG. 2A is a block diagram illustrating a configuration of a processor according to an example embodiment.

FIG. 2A is a block diagram illustrating a configuration of a processor 130 according to an example embodiment.

The processor 130 may be electrically connected to the light source 110 and the image sensor 120. The processor 130 may control the light source 110 and the image sensor 120 at the request of the user. The processor 130 may control the light source 110 and/or the image sensor 120 by using a preset operating condition for the light source 110 and/or a preset operating condition for the image sensor 120. In this case, the operating condition for the light source 110 may include information related to current intensity, duration, and the like, of the light source 110. The operating condition for the image sensor 120 may include information related to a scan delay ($T_b$ in FIG. 3B) between pixel-rows, exposure time ($T_a$ in FIG. 3B) of each pixel-row, a time interval ($T_{f2f}$ in FIG. 3B) between image frames, and the like. In this case, the operating condition for the light source 110 and/or the operating condition for the image sensor 120 may be adjusted according to the type of biological information (e.g., blood pressure, short-term pulse variation, or the like) to be estimated. Alternatively, the processor 130 may perform calibration for each user to preset a personalized operating condition for each user. Based on receiving image frame data from the image sensor 120, the processor 130 may perform preprocessing including filtering, smoothing, and the like, of the image frame data.

The processor 130 may acquire a photoplethysmogram (PPG) signal by using the image frame data obtained from the image sensor 120. The processor 130 may select a predetermined number of pixel-rows from the pixel-rows of the image sensor 120, and acquire the PPG signal of the user on the basis of signal intensities detected in the selected pixel-rows.

For example, a pixel-row selector 210 may calculate a signal-to-noise ratio (SNR) of each pixel-row in the image frame. The pixel-row selector 210 may calculate SNRs based on signals of each pixel-row over the entire image frames. However, various embodiments of the present disclosure are not limited thereto, and the SNRs may be calculated based on signals of each pixel-row in some image frames among the acquired image frames.

The pixel-row selector 210 may select a predetermined number of pixel-rows based on the calculated SNRs. For example, the pixel-row selector 210 may select a predetermined number of pixel-rows in the ascending or descending order of the magnitudes of the SNR. In another example, the pixel-row selector 210 may select all pixel-rows whose SNR exceeds a threshold, or when the number of pixel-rows having an SNR that exceeds the threshold is greater than or equal to a predetermined number, the pixel-row selector 210 may select a predetermined number of pixel-rows in the ascending or descending order of the magnitudes of the SNR from among the pixel-rows having an SNR that exceeds the threshold. In this case, when the number of pixel-rows having an SNR that exceeds the threshold is less than or equal to the predetermined number, the threshold for the SNR may be reset to select a predetermined number of pixel-rows.

The predetermined number of pixel-rows selected by the pixel-row selector 210 may vary for each measurement of biological information according to the user's designation, the type of biological information to be estimated, and the SNR magnitude distribution of each pixel-row.

Figure 3C:
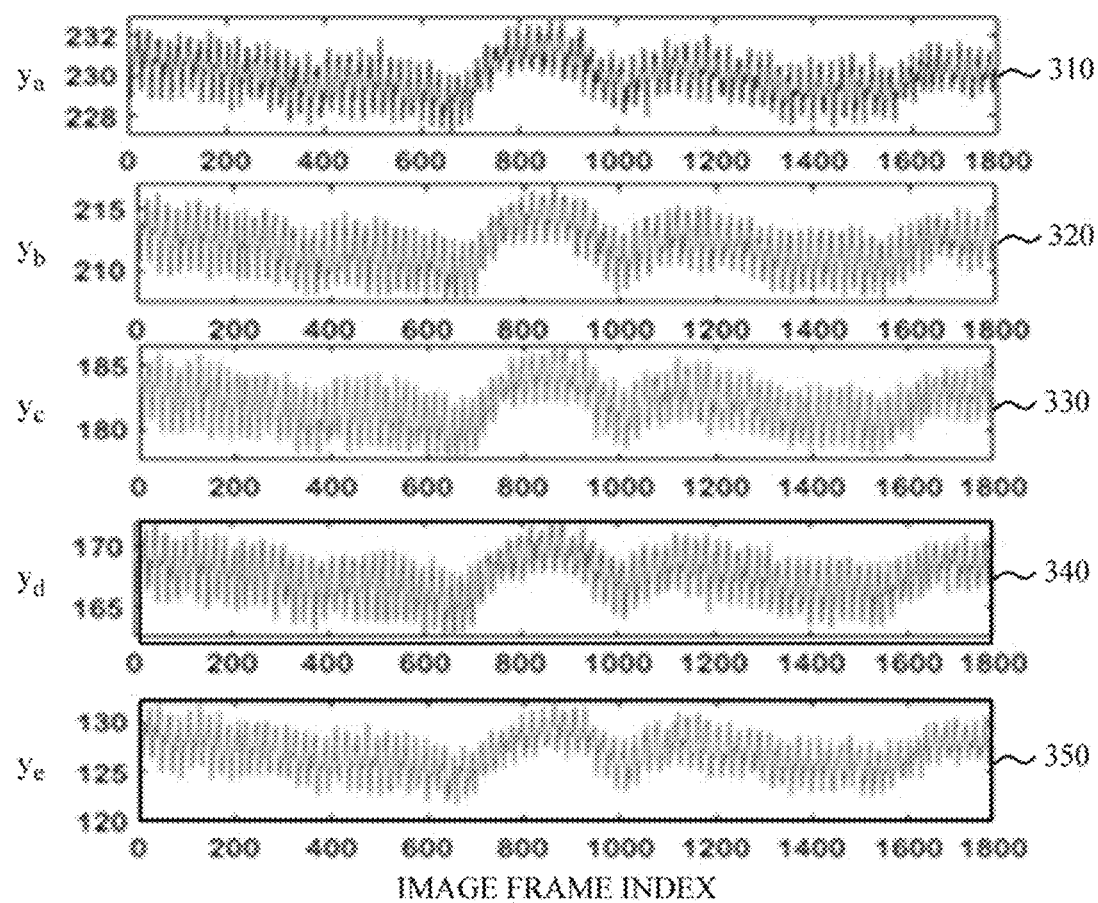
FIG. 3C illustrates a predetermined number of pixel-rows selected from pixel-rows of an image sensor and a signal intensity in each row.

The predetermined number of pixels-rows selected by the processor 130 and signal intensity in each selected pixel-row are shown in FIG. 3C.

In FIG. 3C, signals 310, 320, 330, 340, and 350 detected in five pixel-rows a, b, c, d, and e selected by the pixel-row selector 210 based on the SNR of each pixel-row. In this case, the signal intensities detected in the respective pixel-rows are $y_a$, $y_b$, $y_c$, $y_d$, and $y_e$, each of which represents an average value of signal intensities detected by a plurality of pixels of each row a, b, c, d, and e for each image frame.

A signal intensity corrector 220 may correct the signal intensity detected in the selected pixel-row for each image frame.

A distance between the light source 110 and each pixel-row of the image sensor 120 varies for each pixel-row, and this difference affects the signal intensity detected in each pixel-row. In this case, the signal intensity corrector 220 may correct the difference in signal intensity between the pixel-rows by using Lambert-Beer's law.

Figure 4:
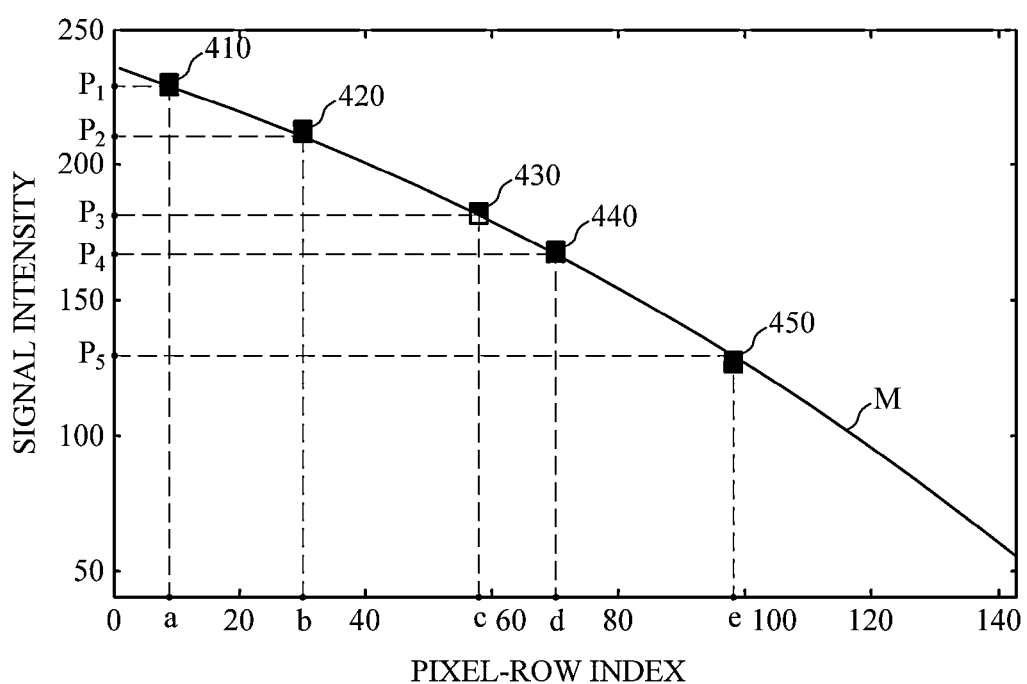
FIG. 4 illustrates corrected signal intensities in a selected predetermined number of pixel-rows and a generated signal intensity compensation model.

The signal intensity corrector 220 may generate a signal intensity compensation model representing the relationship between the corrected signal intensity and the pixel-row number, which is illustrated in FIG. 4.

FIG. 4 illustrates corrected signal intensities in a selected predetermined number of pixel-rows and a generated signal intensity compensation model. Referring to FIG. 4, points 410, 420, 430, 440, and 450 that have, respectively, x-axis values corresponding to the numbers a, b, c, d, and e of pixel-rows selected in one image frame and y-axis values corresponding to values $P_1$, $P_2$, $P_3$, $P_4$, and $P_5$ obtained by correcting signal intensities detected in the selected pixel-rows by using Lambert-Beer's law, and a signal intensity compensation model M generated based on the points 410, 420, 430, 440, and 450 are illustrated. In FIG. 4, it is illustrated that the signal intensity corrector 220 generates, based on each point 410, 420, 430, 440, and 450, a second-order exponential model with a root mean square error (RMSE) of 1.33 and the coefficient of determination (R square) of 0.66 as the signal intensity correction model M.

A PPG signal acquirer 230 may combine the corrected signal intensities for each frame by using a multi-row combine with amplitude compensation (MRAC) algorithm. In this case, the MRAC algorithm may be performed by using the generated signal intensity compensation model and a value obtained by normalizing the corrected signal intensity. The normalization of the corrected signal intensity is shown in Equation 1 below. In Equation 1, $\overline{y_k}$ denotes a normalized value of corrected signal intensities for a k pixel row, $\mu(y_k)$ denotes an average value of the corrected signal intensities for the k pixel-row, and $\sigma(y_k)$ denotes the standard deviation of the corrected signal intensities for the k pixel-row.

$$\overline{y_k} = \frac{y_k - \mu(y_k)}{\sigma(y_k)} \quad (1)$$

The PPG signal acquirer 230 may combine the corrected signal intensities for each frame using an MRAC model as shown in Equation 2 below.

$$Y(j) = \psi \cdot (a \cdot e^{b \cdot \overline{y}(k,n)} + c \cdot e^{d \cdot \overline{y}(k,n)} + \ldots + (1-\psi) \cdot Y(j-1)) \quad (2)$$

Here, Y(j) denotes PPG signal intensities combined using the MRAC model, n denotes an image frame index, $a \cdot e^{b \cdot \overline{y}(k,n)} + c \cdot e^{d \cdot \overline{y}(k,n)}$ denotes the generated signal intensity compensation model, and a, b, c, and d are coefficients of the signal intensity compensation model. $\psi(0 \ll 1)$ denotes a weighting parameter, which is calculated by Equation 3 below. In Equation 3 below, $\Delta T$ denotes a sampling time interval and i is a constant.

$$\psi = 1 - e^{-\Delta T/\tau} \quad (3)$$

A time information acquirer 240 may acquire time information based on operating information of each pixel-row of the image sensor 120. That is, the time information acquirer 240 may receive information on a scan delay time ($T_b$ in FIG. 3B) between the pixel-rows in the image sensor 120 and a time interval between frames ($T_{f2f}$ in FIG. 3B) and acquire time information of the PPG signal based on the received information. Also, the time information acquirer 240 may calibrate the time information by applying PWM on the light source.

Figure 5A:
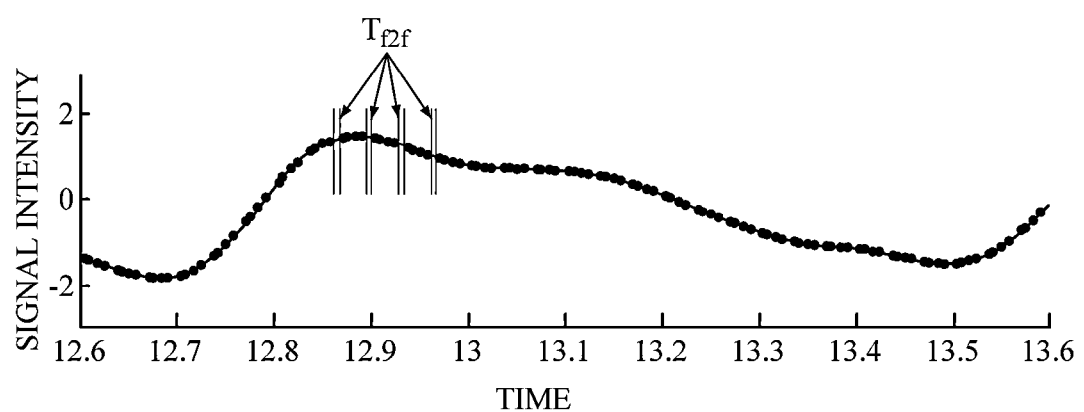
FIG. 5A shows a photoplethysmogram (PPG) signal obtained by combining corrected signal intensities for each image frame.

The PPG signal acquirer 230 may acquire the PPG signal based on the time information acquired by the time information acquirer 240 and the signal intensities of the image frame combined using the MRAC model. The acquired PPG signal is illustrated in FIG. 5A. FIG. 5A shows a PPG signal obtained by combining corrected signal intensities for each image frame.

Figure 5B:
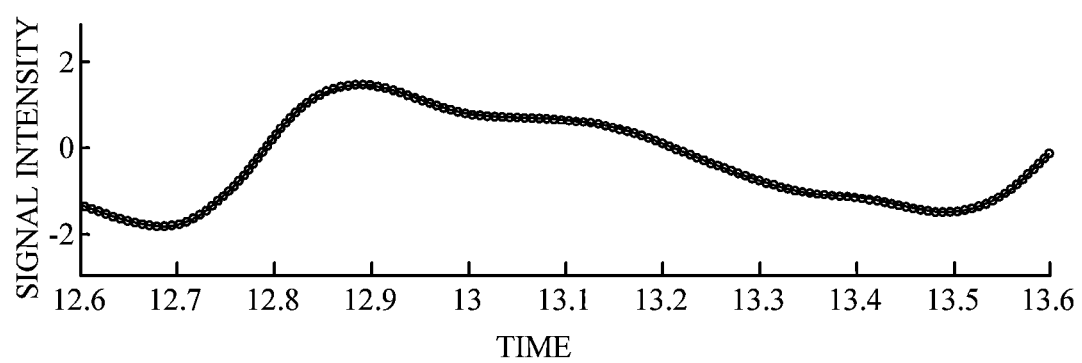
FIG. 5B illustrates a result of re-sampling an obtained PPG signal.

Referring to FIG. 5A, the PPG signal acquired by the PPG signal acquirer 230 is obtained by combining the corrected signal intensities of each frame with the signal intensity compensation model on a frame-by-frame basis, and it can be seen that since the CMOS sensor is blocked during the time interval $T_{f2f}$ between the frames as described above, the signal intensity is not measured during the time interval $T_{f2f}$ between the frames. The processor 130 may acquire a uniform signal as shown in FIG. 5B by resampling the PPG signal shown in FIG. 5A. The processor 130 may perform filtering to reduce residual noise of low intensity in the obtained PPG signal.

A biological information estimator 250 may extract characteristic points based on the acquired PPG signal and estimate biological information based on the extracted characteristic points. The characteristic points extracted based on the acquired PPG signal are illustrated in FIGS. 6A to 6C.

Figure 6A:
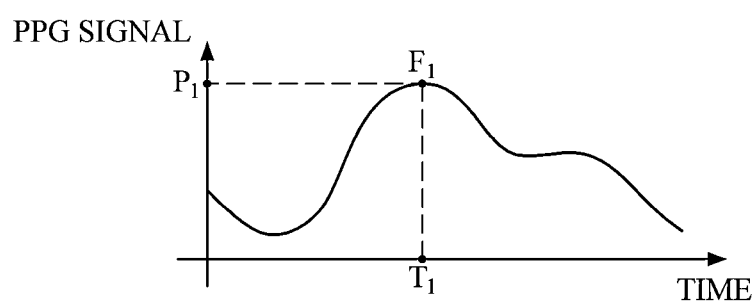
FIGS. 6A to 6C illustrate feature points extracted based on an obtained PPG signal.

Referring to FIG. 6A, the PPG signal has a maximum value $P_1$ at time $T_1$. In this case, the biological information estimator 250 may extract a point F1 at which the PPG signal has the maximum value within a time range during which the PPG signal is acquired, and estimate biological information based on time $T_1$ and/or amplitude $P_1$ of the extracted characteristic point F1.

Figure 6B:
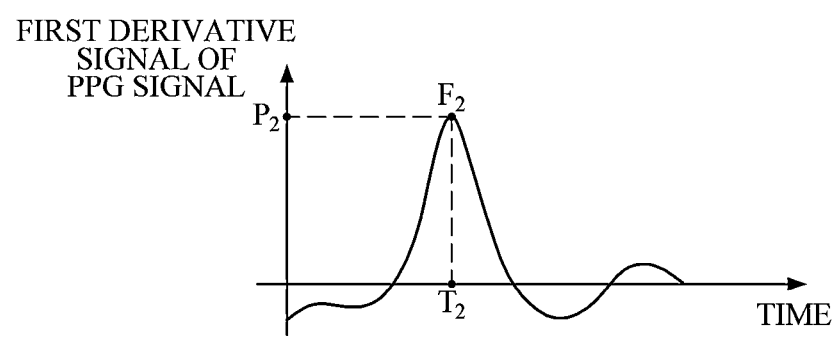

Referring to FIG. 6B, a first derivative signal of the acquired PPG signal has a maximum value $P_2$ at time $T_2$. In this case, the biological information estimator 250 may extract, as a characteristic point, a point $F_2$ at which the first derivative signal of the PPG signal has the maximum value, and estimate biological information based on time $T_2$ and intensity of the extracted characteristic point $F_2$ and/or the amplitude of the PPG signal corresponding to time $T_2$.

Figure 6C:
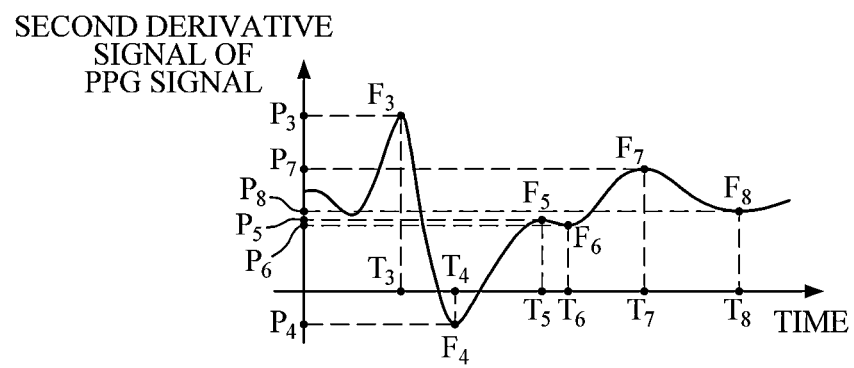

Referring to FIG. 6C, the biological information estimator 250 may extract at least one of an a-wave peak point $F_3$, a b-wave valley point $F_4$, a c-wave peak point $F_5$, and a d-wave valley point $F_6$, an e-wave peak point $F_7$, or a diastolic peak point $F_8$ of a second derivative signal of the PPG signal as a characteristic point, and estimate biological information based on times $T_3$, $T_4$, $T_5$, $T_6$, $T_7$, and $T_8$ and intensities $P_3$, $P_4$, $P_5$, $P_6$, $P_7$, and $P_8$ of the extracted characteristic points and/or the amplitude of the PPG signal corresponding to each of times $T_3$, $T_4$, $T_5$, $T_6$, $T_7$, and $T_8$.

However, the present disclosure is not limited thereto, and an entire area or partial area of the PPG signal may be further included.

The biological information estimator 250 may combine two or more of the extracted characteristic points to obtain a feature for estimating biological information and may estimate biological information by applying a predefined biological information estimation model as represented by Equation 4 below. The biological information estimation model may be defined as various linear and/or non-linear combination functions, such as addition, subtraction, division, multiplication, logarithmic value, regression equation, and the like, with no specific limitation. For example, the following Equation 4 represents a simple linear equation.

$$y=ax+b \quad (4)$$

In Equation 4, y denotes biological information to be detected such as, for example, oxygen saturation SpO2, pulse rate variability, blood pressure, arterial stiffness, stress index, body fat, body temperature, and the like. A value of x represents an acquired feature. a and b are coefficients for weighting a feature value and may be fixed values universally applicable to a predefined plurality of users according to the type of biological information. Alternatively, a and b may be values adjusted for each user according to the user's characteristics.

The apparatus 100 for estimating biological information may further include a force sensor for measuring a contact force when the object comes in contact with and applies force to a contact surface of the image sensor 120. When the force sensor measures a force at each measurement time, the processor 130 may estimate blood pressure based on oscillometry on the basis of the acquired PPG signal and the contact force as described above.

Figure 2B:
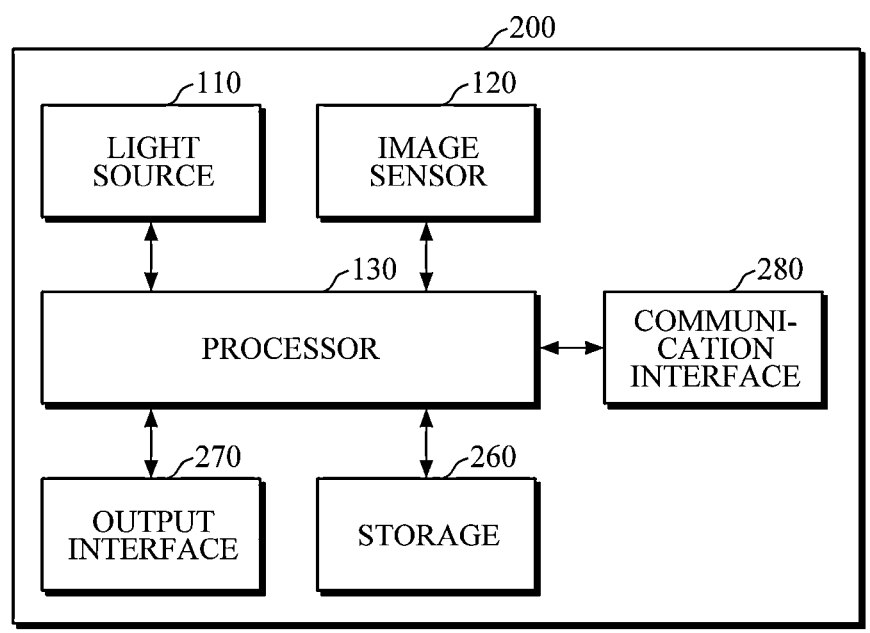
FIG. 2B is a block diagram illustrating an apparatus for estimating biological information according to another example embodiment.

FIG. 2B is a block diagram illustrating an apparatus 200 for estimating biological information according to another example embodiment.

Referring to FIG. 2B, an apparatus 200 for estimating biological information may further include a storage 260, an output interface 270, and a communication interface 280 in addition to a light source 110, an image sensor 120, and a processor 130. Hereinafter, since the light source 110, the image sensor 120, and the processor 130 are described above, description will be made with focus on the storage 260, the output interface 270, and the communication interface 280.

The storage 260 may store operating information of the image sensor 120, and processing results of the image sensor 120 and/or the processor 130. Also, the storage 260 may store various types of reference information to be used for estimating biological information. For example, the reference information may include user characteristic information, such as a user's age, gender, health condition, and the like. In addition, the reference information may include information, such as a biological information estimation model, biological information estimation criteria, and the like, but is not limited thereto. In another example, the storage 260 may store operating information regarding ISO of the image sensor 120, the exposure time of each pixel, white balance, output resolution, camera focus, and the like.

In this case, the storage 260 may include at least one storage medium of a flash memory type memory, a hard disk type memory, a multimedia card micro type memory, a card type memory (e.g., a secure digital (SD) memory, an extreme digital (XD) memory, etc.), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like, but is not limited thereto.

The output interface 270 may output successive image frames acquired by the image sensor 120, a predetermined number of pixel-rows selected by the processor 130, an acquired PPG signal, and an estimated biological information value and/or guide information. For example, the output interface 270 may output data processed by the image sensor 120 or the processor 130 by a visual method using a display module, or by a non-visual method through voice, vibration, tactile sensation, or the like, using a speaker, a haptic module, and the like. In this case, the output interface 170 may divide a display area into two or more areas, in which the output interface 170 may output the acquired PPG signal, the contact force between the image sensor 120 and an object, and the like, in various forms of graphs in a first area; and may output an estimated biological information value in a second area. At this time, in response to the estimated biological information value falling outside of a normal range, the output interface 170 may output warning information in various manners, such as highlighting an abnormal value in red, and the like, displaying the abnormal value along with a normal range, outputting a voice warning message, adjusting a vibration intensity, and the like.

In addition, the output interface 270 may output guide information related to a position of an object, which is generated by the processor 130. For example, the output interface 270 may output the guide information by a visual method using a display module, or by a non-visual method through voice, vibration, tactile sensation, and the like, using a speaker, a haptic module, or the like. For example, the output interface 270 may visually display the guide information such that the user adjusts the position of the object vertically or horizontally according to the positions of the light source 110 and the image sensor 120.

The output interface 270 may provide information related to the accuracy of biological information estimation to the user by providing values of the root mean square error and coefficient of determination of the signal intensity compensation model (M in FIG. 4) generated by the signal intensity corrector (220 in FIG. 2A) of the processor 130.

The communication interface 280 may communicate with an external device using wired/wireless communication technologies under the control of the processor 130 and transmit and receive a variety of data. For example, the communication interface 280 may transmit a biological information estimation result to the external device and receive various pieces of reference information to estimate biological information from the external device. The external device may include an information processing device, such as a cuff-type blood pressure measurement device, a smartphone, a tablet PC, a desktop PC, a laptop PC, or the like.

The communication technology may include Bluetooth communication, Bluetooth low energy (BLE) communication, near field communication (NFC), wireless local area network (WLAN) communication, ZigBee communication, infrared data association (IrDA) communication, wireless fidelity (Wi-Fi) direct (WFD) communication, ultra-wideband (UWB) communication, Ant+ communication, Wi-Fi communication, radio frequency identification (RFID) communication, 3rd generation (3G) communication, 4G communication, 5G communication, etc. However, the communication technology is not limited to the above examples.

Figure 7:
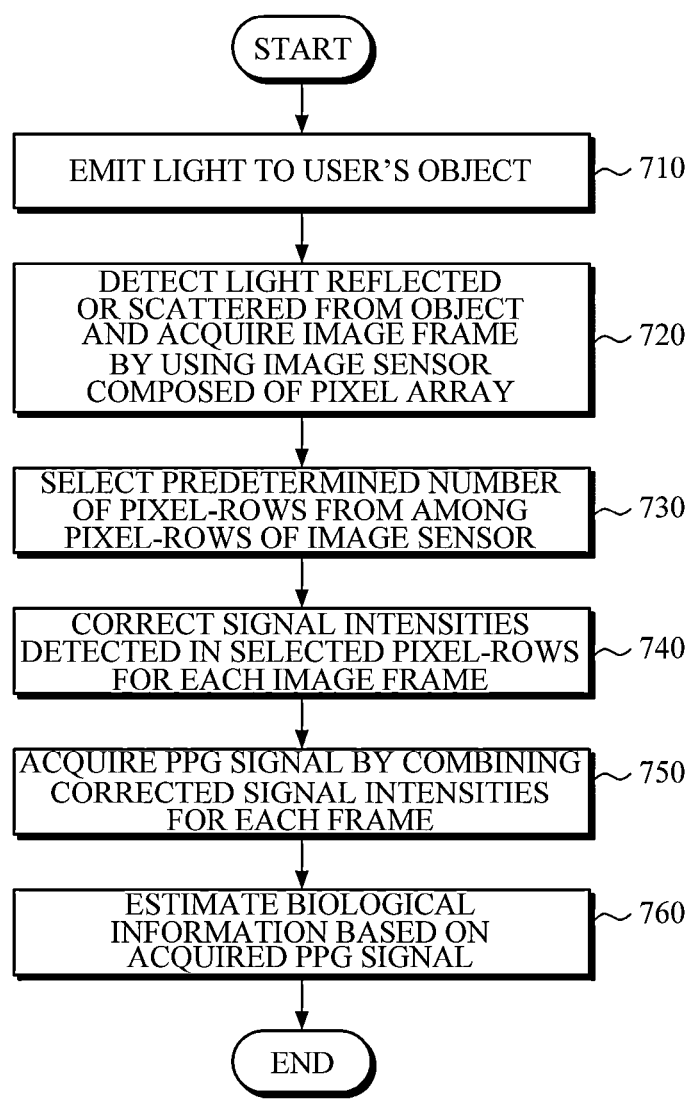
FIG. 7 is a flowchart illustrating a method of estimating biological information according to an example embodiment.

FIG. 7 is a flowchart illustrating a method of estimating biological information according to an example embodiment.

The embodiment shown in FIG. 7 may be one example of a blood pressure estimation method performed by the apparatuses 100 and 200 of FIGS. 1 to 2B, which is described above in detail, such that description thereof will be briefly made.

Light may be emitted to an object of a user in operation 710. The light emitted to the object may include visible light, infrared light, near infrared light, etc.

Then, light scattered or reflected from the object may be detected and image frames may be acquired by using an image sensor composed of a pixel array. The image frames may be acquired using a rolling shutter technique. After the image frames are acquired, preprocessing including filtering of image frame data may be carried out.

Subsequently, a predetermined number of pixel-rows may be selected from pixel-rows of the image sensor in operation 730. An SNR of each pixel-row in the image frame may be calculated, and a predetermined number of pixel-rows may be selected based on the calculated SNR. In this case, SNRs may be calculated based on signals of each pixel-row over the entire image frames. However, various embodiments of the present disclosure are not limited thereto, and the SNRs may be calculated based on signals of each pixel-row in some image frames among the acquired image frames.

In addition, the predetermined number of pixel-rows may be selected according to the calculated magnitudes of the SNR. Pixel-rows having an SNR that exceeds a threshold may be all selected, or a predetermined number of pixel-rows may be selected in an ascending or descending order of the magnitudes of the SNR without setting the threshold.

Then, signal intensities detected in the selected pixel-rows for each image frame may be corrected in operation 740. A difference in signal intensity between the pixel-rows may be corrected using Lambert-Beer's law. Also, a signal intensity compensation model representing the relationship between the corrected signal intensity and the pixel-row number may be generated.

Then, a PPG signal may be acquired by combining the corrected signal intensities for each image frame in operation 750. In this case, the corrected signal intensities for each frame may be combined with each other using the generated signal intensity compensation model and an MRAC algorithm. A PPG signal may be acquired based on the signal intensities of the image frame combined using the MRAC model and acquired time information. In addition, the MRAC algorithm may be performed by using the generated signal intensity compensation model and a value obtained by normalizing the corrected signal intensity.

Then, biological information may be estimated based on the acquired PPG signal in operation 760. In this case, a characteristic point may be extracted based on the PPG signal, and the biological information may be estimated based on the extracted characteristic point. The characteristic point may be extracted based on the acquired PPG signal, a first derivative signal of the PPG signal, and a second derivative signal of the PPG signal. In addition, the biological information may be estimated by applying a biological information estimation model predefined based on the extracted characteristic point.

Figure 8:
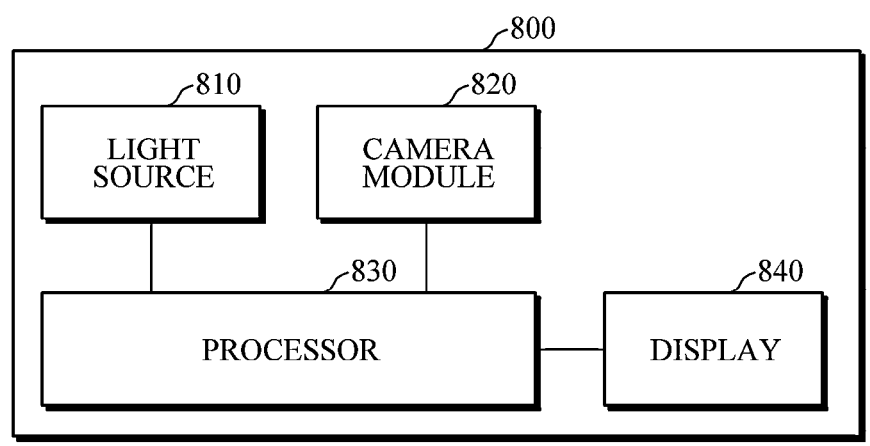
FIG. 8 is a block diagram illustrating an electronic device according to an example embodiment.

FIG. 8 is a block diagram illustrating an electronic device according to an example embodiment.

Referring to FIG. 8, an electronic device 800 according to an exemplary embodiment includes a light source 810, a camera module 820, a processor 830, and a display 840. The electronic device 800 according to an example embodiment may include at least one of a smartphone, a mobile phone, a wearable device, a wrist watch, various medical devices (e.g., a short-wave infrared camera, a long-wave infrared camera, etc.), or a combination thereof. The electronic device 800 may include a main body.

The light source 810 may be disposed on one surface of the main body and emit light to an object. In addition, the light source 810 may be turned on all the time in the process of estimating biological information, or may be driven in a pulse width modulation (PWM) scheme, under the control of the processor 830.

The processor 830 may be disposed inside the main body, and electrically connected to the light source 810 and the camera module 820. The processor 830 may control the light source 810 and the camera module 820 at the request of the user. Also, the processor 830 may acquire a PPG signal by using image frame data obtained from an image sensor.

The camera module 820 may be disposed on one surface of the main body and include the image sensor composed of a pixel array. The image sensor may be a CMOS image sensor. The image sensor may acquire successive image frames by detecting light scattered or reflected from an object using a rolling shutter technique. A camera lens of the camera module 820 may include at least one of a standard lens, a super wide-angle lens, a wide-angle lens, a telephoto lens, a macro lens, or a zoom lens.

The camera module 820 may include a plurality of image sensors. For example, the camera module 820 may include a plurality of front camera image sensors, a plurality of rear camera image sensors, or one or more front camera image sensors and one or more rear camera image sensors. The plurality of image sensors may acquire image frames for one object, and acquire image frames for different objects.

In this case, when a plurality of image sensors acquires an image frame for one object (e.g., a plurality of front cameras photograph a user's index finger), the processor 830 may select one from among PPG signals obtained based on each image frame acquired by the plurality of image sensors on the basis of an RMSE or a coefficient of decision (R Square), and may estimate biological information based on the selected PPG signal.

In another example, when a plurality of image sensors acquire image frames for different objects (e.g., a front camera photographs the user's index finger and a rear camera photographs the user's wrist), the processor 830 may estimate a plurality of biological information on the basis of a plurality of PPG signals obtained based on a plurality of image frames.

The display 840 may provide the user with a biological information estimation result, an accuracy value of biological information estimation, and guide information related to a position of a subject in a visual and/or non-visual manner.

Figure 9:
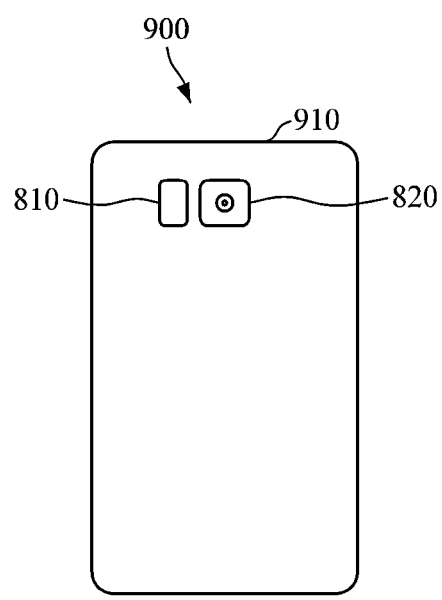
FIG. 9 illustrates a smart device according to an example embodiment.

FIG. 9 illustrates a smart device 900 as an example embodiment of the electronic device 800 of FIG. 8. The smart device may include a smartphone, a tablet PC, and the like. However, the electronic device 800 of FIG. 8 is not limited to examples of the illustrated smart device, and may include a smart watch wearable device, and the like.

Referring to FIG. 9, a smart device 900 may include a light source 810 disposed on one surface of a main body 910. The light source 810 may emit light to an object, and a processor 830 may control the light source 810. The object may be positioned vertically or horizontally according to the positions of the light source 810 and the camera module 820.

The camera module 820 may be disposed on one surface of the main body 910, and may include an image sensor composed of a pixel array. The image sensor may be a CMOS image sensor. The image sensor may acquire successive image frames by detecting light scattered or reflected from an object using a rolling shutter technique. The camera module 820 may be in contact with the user's object and acquire image frames of the object, and may acquire image frames of the object through light reflected from the object without contacting the object.

The processor 830 may be mounted in the main body 910, and may estimate biological information, such as oxygen saturation (SpO2), pulse rate variability, blood pressure, arterial stiffness, stress index, body fat, body temperature, and the like, based on biological information estimated by the image sensor included in the camera module 820.

In addition, the display 840 may include a display disposed on a front surface of the main body 910. The display may include a touch screen for touch input.

In addition, a communication interface for wired/wireless communication with an external device, a manipulator for receiving a user's command and transmitting the command to the processor 830, and the like, may be mounted in the main body 910. Various other modules for perming various function may be mounted in the main body 910.

The example embodiments can be implemented by computer-readable code stored on a non-transitory computer-readable medium and executed by a processor. Code and code segments constituting the computer program can be inferred by a computer programmer skilled in the art. The computer-readable medium includes all types of record media in which computer-readable data are stored. Examples of the computer-readable medium include a ROM, a RAM, a CD-ROM, a magnetic tape, a floppy disk, and an optical data storage. Further, the computer-readable medium may be implemented in the form of a carrier wave such as Internet transmission. In addition, the computer-readable medium may be distributed to computer systems over a network, in which computer readable code may be stored and executed in a distributed manner.

A number of example embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating biological information of a user, the apparatus comprising:
    a light source configured to emit light to an object of the user;
    an image sensor comprising a pixel array, and configured to acquire successive image frames by detecting light scattered or reflected from the object of the user; and
    a processor configured to:
        select a predetermined number of pixel-rows from among pixel-rows of the image sensor,
        detect signal intensities in the predetermined number of pixel-rows for each image frame of the successive image frames,
        correct the signal intensities,
        combine the signal intensities for each image frame of the successive image frames based on correcting the signal intensities,
        acquire a photoplethysmogram (PPG) signal based on combining the signal intensities, and
        estimate the biological information of the user based on the PPG signal,
    wherein the processor is configured to correct the signal intensities by compensating for an influence, on a signal intensity, by a distance between the light source and each of the predetermined number of pixel-rows of the image sensor by using Lambert-Beer's law.

2. The apparatus of claim 1, wherein the processor is configured to calculate a signal-to-noise ratio (SNR) of each pixel-row of the image frame, and select the predetermined number of pixel-rows based on the SNR of each pixel-row of the image frame.

3. The apparatus of claim 2, wherein the processor is configured to select the predetermined number of pixel-rows in an ascending order or a descending order of magnitudes of the SNR of each pixel-row of the image frame.

4. The apparatus of claim 1, wherein the processor is configured to generate a signal intensity compensation model representing a relationship between the signal intensities and a pixel-row number.

5. The apparatus of claim 4, wherein the processor is configured to combine the signal intensities for each frame by using the signal intensity compensation model and a multi-row combine with amplitude compensation (MRAC) algorithm.

6. The apparatus of claim 5, wherein the processor is configured to acquire time information based on operating information of each pixel-row of the image sensor, and acquire the PPG signal based on the signal intensities of each image frame and the time information.

7. The apparatus of claim 1, wherein the processor is configured to resample the PPG signal, or perform preprocessing to reduce noise by using a filter.

8. The apparatus of claim 1, wherein the processor is configured to extract feature points based on the PPG signal, and estimate the biological information based on the feature points.

9. The apparatus of claim 1, wherein the biological information comprises at least one of oxygen saturation (SpO2), pulse rate variability, blood pressure, arterial stiffness, stress index, body fat, or body temperature.

10. A method of estimating biological information of a user, the method comprising:
    emitting, by a light source, light to an object of the user;
    detecting, by an image sensor comprising a pixel array, light scattered or reflected from the object of the user;
    acquiring, by the image sensor, successive image frames based on detecting the light scattered or reflected from the object of the user;
    selecting, by a processor, a predetermined number of pixel-rows from among pixel-rows of the image sensor;
    detecting, by the processor, signal intensities in the predetermined number of pixel-rows for each image frame of the successive image frames;
    correcting, by the processor, the signal intensities;
    combining, by the processor, the signal intensities for each image frame of the successive image frames based on correcting the signal intensities;
    acquiring, by the processor, a photoplethysmogram (PPG) signal based on combining the signal intensities; and
    estimating, by the processor, the biological information of the user based on the PPG signal,
    wherein the correcting comprises correcting the signal intensities by compensating for an influence, on a signal intensity, by a distance between the light source and each of the predetermined number of pixel-rows of the image sensor by using Lambert-Beer's law.

11. The method of claim 10, wherein the selecting of the predetermined number of pixel-rows comprises:
    calculating a signal-to-noise ratio (SNR) of each pixel-row of the image frame; and
    selecting the predetermined number of pixel-rows based on the SNR of each pixel-row of the image frame.

12. The method of claim 11, wherein the selecting of the predetermined number of pixels-rows based on the SNR comprises selecting the predetermined number of pixels-rows in an ascending order or a descending order of magnitudes of the SNR of each pixel-row of the image frame.

13. The method of claim 10, further comprising generating a signal intensity compensation model representing a relationship between the signal intensities and a pixel-row number.

14. The method of claim 13, wherein the acquiring of the PPG signal by combining the signal intensities for each frame comprises combining the signal intensities for each frame by using the signal intensity compensation model and a multi-row combine with amplitude compensation (MRAC) algorithm.

15. The method of claim 14, wherein the acquiring of the PPG signal comprises
acquiring time information based on operating information of each pixel-row of the image sensor; and
acquiring the PPG signal based on the signal intensities of each image frame and the acquired time information.

16. An electronic device comprising:
a main body;
a light source disposed on a surface of the main body, and configured to emit light to an object of a user;
a camera module disposed on the surface of the main body, and comprising an image sensor configured to acquire an image frame by detecting light reflected or scattered from the object; and
a processor disposed in the main body, and configured to:
select a predetermined number of pixel-rows from among pixel-rows of the image sensor,
detect signal intensities in the predetermined number of pixel-rows for each image frame of successive image frames,
correct the signal intensities,
combine the signal intensities for each image frame of the successive image frames based on correcting the signal intensities,
acquire a photoplethysmogram (PPG) signal based on combining the signal intensities, and
estimate biological information of the user based on the PPG signal,
wherein the processor is configured to correct the signal intensities by compensating for an influence, on a signal intensity, by a distance between the light source and each of the predetermined number of pixel-rows of the image sensor by using Lambert-Beer's law.

17. The electronic device of claim 16, wherein the image sensor is configured to acquire an image frame using a rolling shutter technique.

18. The electronic device of claim 16, wherein the processor is configured to control the light source to be turned on while the image sensor acquires the image frame, or control the light source using a pulse width modulation scheme.

* * * * *